US009617383B2

(12) United States Patent
Chan et al.

(10) Patent No.: US 9,617,383 B2
(45) Date of Patent: Apr. 11, 2017

(54) PEG-BASED MICROPARTICLES

(71) Applicant: DNA Medicine Institute, Inc., Cambridge, MA (US)

(72) Inventors: Eugene Y. Chan, Boston, MA (US); Moon Bae, Cambridge, MA (US)

(73) Assignee: DNA Medicine Institute, Inc., Cambridge, MA (US)

( * ) Notice: Subject to any disclaimer, the term of this patent is extended or adjusted under 35 U.S.C. 154(b) by 0 days.

(21) Appl. No.: 14/682,080

(22) Filed: Apr. 8, 2015

(65) Prior Publication Data

US 2015/0284486 A1    Oct. 8, 2015

Related U.S. Application Data

(60) Provisional application No. 61/977,067, filed on Apr. 8, 2014.

(51) Int. Cl.
| | | |
|---|---|---|
| *C08F 2/46* | (2006.01) | |
| *C08G 61/04* | (2006.01) | |
| *C08G 65/48* | (2006.01) | |
| *C08F 290/06* | (2006.01) | |
| *G01N 33/543* | (2006.01) | |
| *G01N 33/545* | (2006.01) | |

(52) U.S. Cl.
CPC .......... *C08G 65/48* (2013.01); *C08F 290/062* (2013.01); *G01N 33/545* (2013.01); *G01N 33/54353* (2013.01)

(58) Field of Classification Search
CPC ..................................................... C08F 120/34
USPC ......................................... 522/167, 1; 520/1
See application file for complete search history.

(56) References Cited

PUBLICATIONS

Mizrahi et al, Novel Poly(ethylene glycol) monomers Bearing Diverse Functional Groups, Oct. 13, 2010, Journal of Polymer Sience: Part A: Polymer Chemistry, 48, 5468-5478.*
Jung et al, Fabrication of Chitosan-Poly(ethylene glycol) Hybrid Hydrogel Microparticles via Replica Molding and its application toward Facile Conjugation of Biomolecules, Nov. 19, 2012, Langmuir, 28, 17061-17070.*
Dendukuri et al, Stop-flow lithrography in microfluidic device, May 21, 2007, Lab Chip, 7, 818-828.*

* cited by examiner

*Primary Examiner* — Ling Choi
*Assistant Examiner* — Jessica E Whiteley
(74) *Attorney, Agent, or Firm* — Danielson Legal LLC

(57) ABSTRACT

Synthesis of monodisperse PEG-based microparticles with stable coupling chemistries. Biomolecules are conjugated to monodisperse PEG microparticles using non-amine chemistries, such as sulfhydryl groups, azide, or alkyne-based chemistries.

6 Claims, 8 Drawing Sheets

PEG-BASED MICROPARTICLES

CROSS-REFERENCE TO RELATED APPLICATIONS

The present application claims the benefit of U.S. provisional application No. 61/977,067, filed on Apr. 8, 2014, the entire disclosure of which is incorporated by reference as if set forth in its entirety herein.

FIELD

The invention relates to the stable coupling of proteins and other biomolecules to polyethylene glycol (PEG) microparticles, and in particular to a novel chemistry for the same.

BACKGROUND

Polyethylene glycol microparticles are highly biocompatible and have numerous advantages over conventional polymeric (polystyrene, latex, etc.) beads. For instance, PEG microparticles have low autofluorescence, are porous, have low non-specific binding, and can have different functionalities. In particular, PEG with reactive acrylate groups can be utilized to form hydrogel particles using ultraviolet (UV) exposure. PEG microparticles thus have desirable attributes for biological applications.

PEG particles are readily formed by UV curing of acrylate functionalized PEG. PEG-monoacrylate (PEGMA) and PEG-diacrylate (PEGDA) are common forms of UV curable PEG. This involves the use of a photoinitiator with an acrylate functionalized PEG mixture. Exposure to UV leads to the initiation of the reaction and thus the formation of the particles.

A common challenge to all PEG microparticles is functionalization. PEGDA or PEGMA does not have amine, sulfhydryl, or other chemical groups that can be readily utilized for attachment of biomolecules. Proteins and other biomolecules without functional groups can be directly polymerized into the PEG without functional groups. The downside of this approach is that the biomolecules may leach out from the PEG matrix since they are not covalently attached. Another downside, particularly for proteins, is that mixing them with PEG leads to protein precipitation. PEG is a common molecule utilized to precipitate proteins for a variety of applications.

One approach to incorporating biomolecules into the PEG matrix includes reacting the protein or biomolecule with a heterobifunctional PEG molecule, such as ACRYL-PEG-SCM, prior to mixing the protein in with the PEG mixture, where SCM stands for succinimidyl carboxymethyl. The SCM group reacts with the amine groups on the proteins, attaching the PEG-acrylate molecule to it and making it more soluble in a PEG mixture. Conventionally, proteins are precipitated in PEG, but this approach allows mixture of the protein with PEG. This approach, however, utilizes significant amounts of protein, as much as 25 µg/µL, which is highly impractical. Furthermore, different types of protein may precipitate in the PEG mixture.

Amine-based chemistries are challenging because they are highly labile. Groups with SCM have half-lives of 0.75 minutes and those with succinimidyl valerate have 33.6 minutes. While these groups can be introduced into the PEG mixture, they will be hydrolyzed by the time the PEG microparticle synthesis is complete and this therefore is not the best solution. Rapid hydrolysis is therefore a hurdle to these chemistries.

At least one group has attempted to add carboxyl groups to the PEG matrix by introducing acrylic acid into the PEG-based mixture. The polymerization of acrylic acid into the particles results in carboxyl groups that can later be functionalized. Conventionally, carboxyl groups can be coupled to amine groups on biomolecules using EDC (1-Ethyl-3-(3-dimethylaminopropyl)carbodiimide) and NHS (N-Hydroxysuccinimide). This chemistry results in amide bond formation between the protein and the hydrogel surface. While this is a common approach for the addition of biomolecules to carboxyl groups, the chemistries are highly sensitive to moisture, requiring them to be stored in dry environments, and even with desiccants the reagents can degrade quickly.

Another impediment to the additional of functional groups to the hydrogels is the commercial availability of heterobifunctional PEG molecules. The commercial stock of various types of heterobifunctional PEG molecules changes with time and thus limits the type of functionalized PEG microparticles that can be fabricated.

For the foregoing reasons, there are significant challenges that need to be overcome in order to create a stable coupling chemistry for PEG-based microparticles.

SUMMARY

Embodiments of the present invention utilize non-amine-based chemistries for biomolecule coupling to PEG microparticles. This approach avoids the hydrolysis issues associated with amine-based chemistries and allows for greater time for washing and manipulation of the microparticles during the coupling steps. The chemistry is stable and allows time for microparticle handling and washing prior to the actual coupling step. Furthermore, a covalent bond is formed between the microparticle and the biomolecule of interest.

In one aspect, embodiments of the present invention relate to a microparticle comprising a polyethylene glycol (PEG) body and a biomolecule, wherein the biomolecule is conjugated to the PEG body using a non-amine chemistry incorporated into the PEG body. The PEG body may be elongated.

In one embodiment, the non-amine chemistry is selected from a group consisting of sulfhydryl groups, thiol reactive, azide-based, or alkyne-based chemistries. Suitable thiol reactive chemistries include maleimide (MAL), vinyl sulfone (VS), iodoacetamide (IA), orthopyridyl disulfide (OPD), ACRYL-PEG-VS, ACRYL-PEG-IA, ACRYL-PEG-OPD, and multi-arm PEG having at least one acryl group and at least one functional group for reacting with a thiol. Suitable azide-based chemistries include ACRYL-PEG-AZ. Suitable alkyne-based chemistries include ACRYL-PEG-ALK.

In another aspect, embodiments of the present invention relate to a method for manufacturing microparticles. The method includes adding a non-amine chemistry to a polyethylene glycol (PEG) prepolymer mixture, mixing the mixture, and applying ultraviolet light to a portion of the mixture to form a polymerized microparticle. In one embodiment, the method further includes washing the polymerized microparticle to remove unpolymerized monomers.

In one embodiment, the method further includes generating microfluidic droplets from the mixture. In one embodiment, the method further includes generating at least one polymerized microparticle using stop-flow lithography. In one embodiment, the method further includes generating at least one polymerized microparticle using continuous-flow lithography. In one embodiment, the method further includes generating at least one polymerized microparticle using a slide-based fabrication process. In one embodiment, the method further includes washing the microparticle with a neutral pH buffer solution.

The foregoing and other features and advantages of the present invention will be made more apparent from the descriptions, drawings, and claims that follow. One of ordinary skill in the art, based on this disclosure, would understand that other aspects and advantages of the present invention exist.

BRIEF DESCRIPTION OF DRAWINGS

In the drawings, like reference characters generally refer to corresponding parts throughout the different views. The drawings are not necessarily to scale, emphasis instead being placed on the principles and concepts of operation.

DETAILED DESCRIPTION

Figure 1:
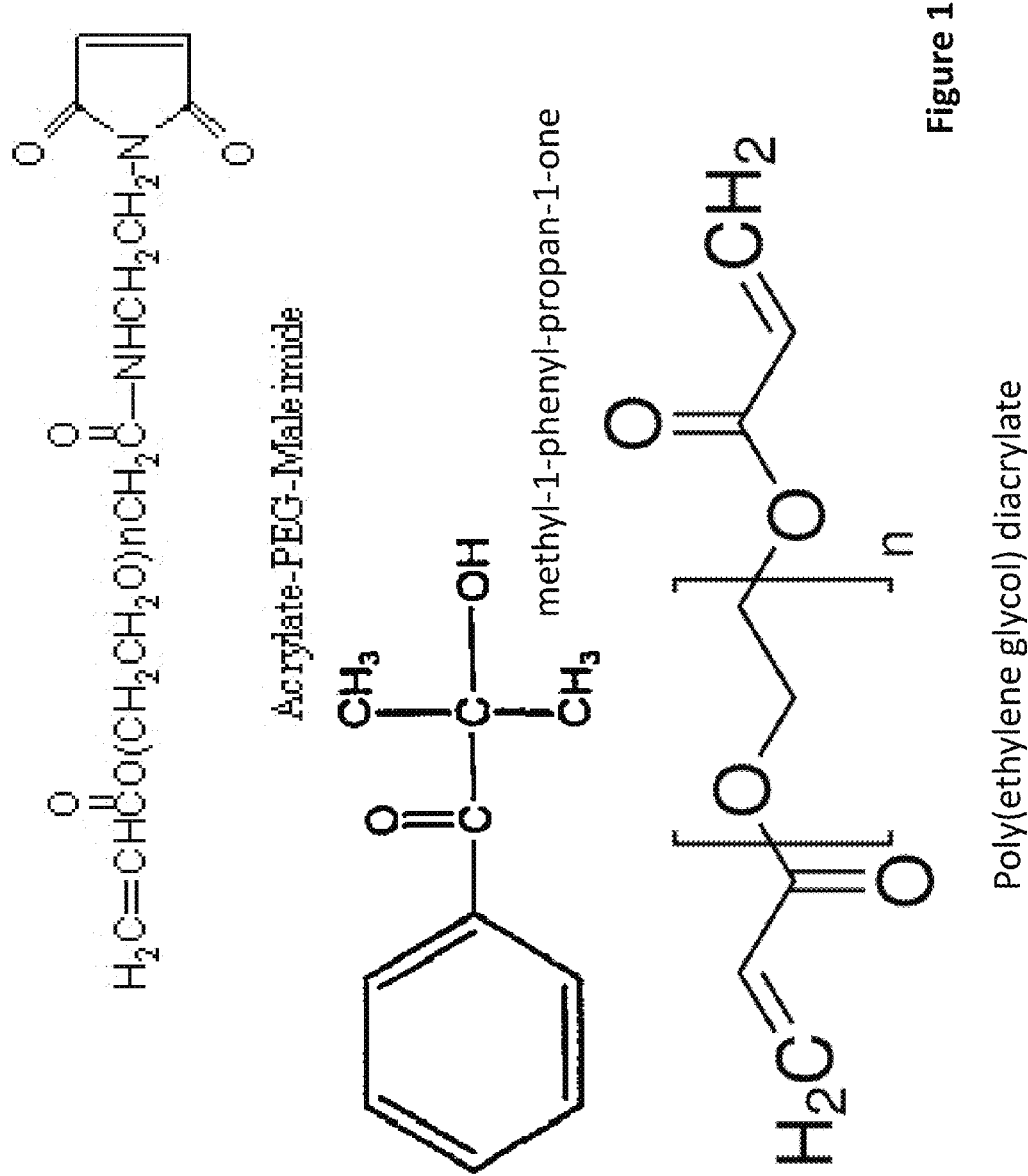
FIG. 1 shows the chemical structures for acrylate-PEG-maleimide, methyl-1-phenyl-propan-1-one, and polyethylene glycol) diacrylate.
Figure 2:
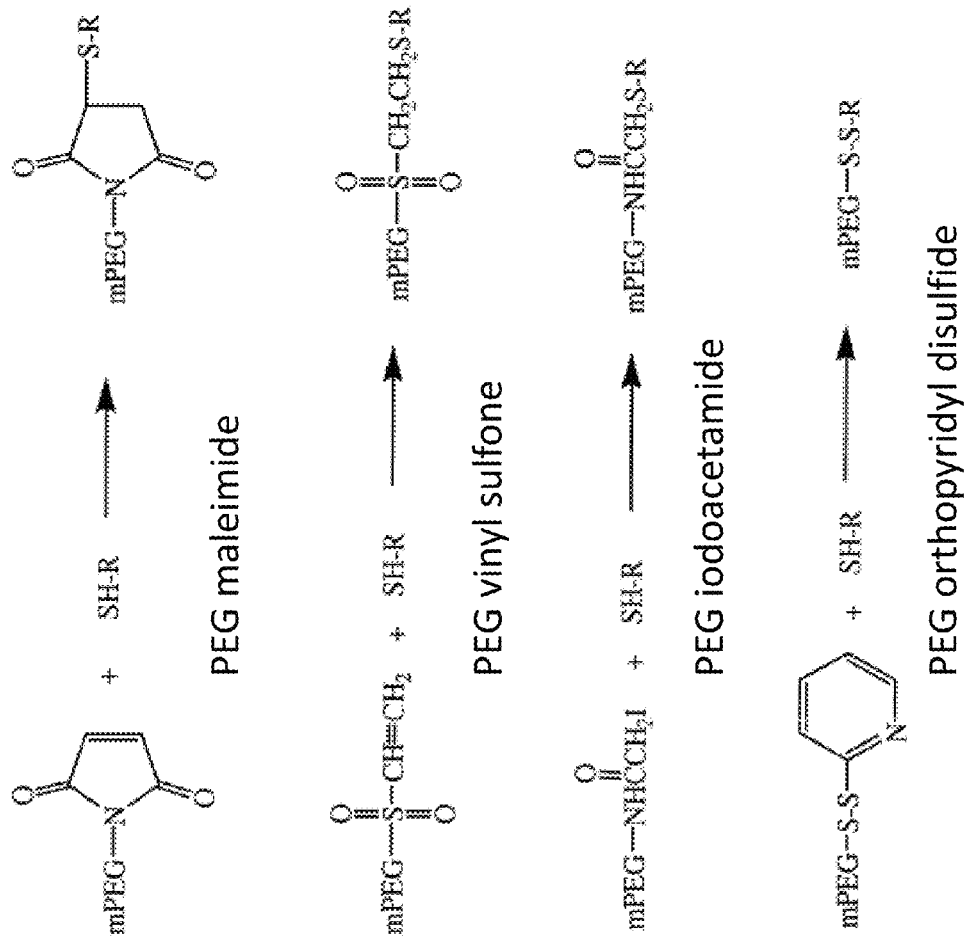
FIG. 2 shows several examples of thiol-reactive groups that are compatible with microparticle synthesis. These include maleimide, vinyl sulfone, iodoacetamide, and orthopyridyl disulfide.
Figure 3:
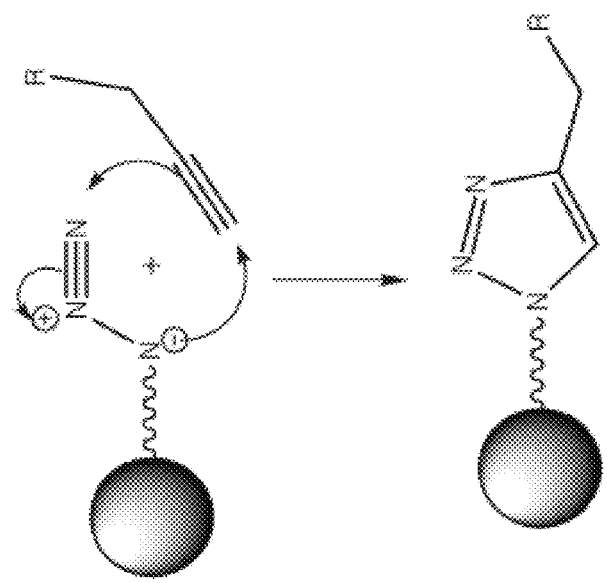
FIG. 3 shows alkyne, azide cycloaddition.
Figure 4:
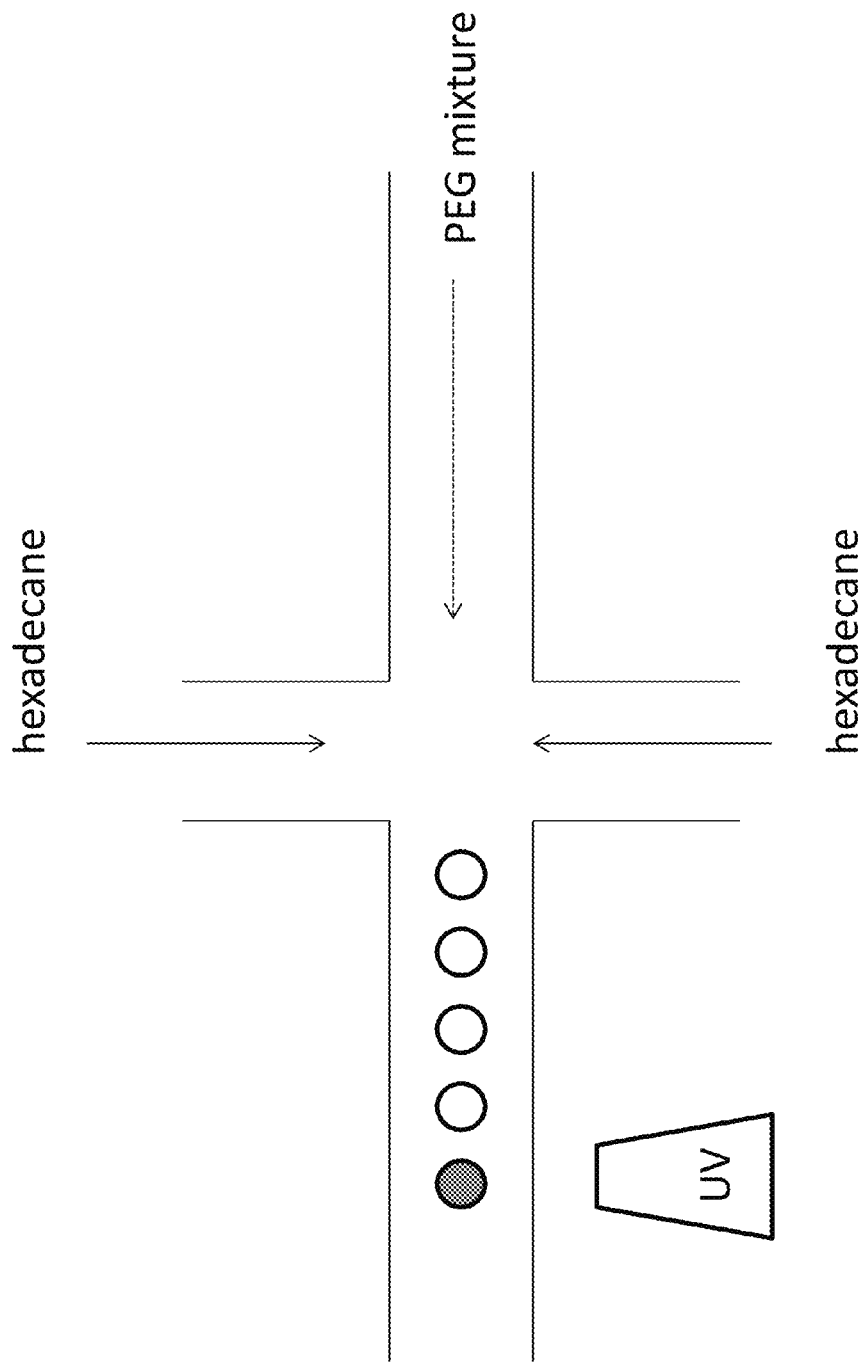
FIG. 4 shows the fabrication of PEG microdroplets by flow focusing through the use of hexadecane, PEG prepolymer mixture, and UV photocuring.
Figure 5:
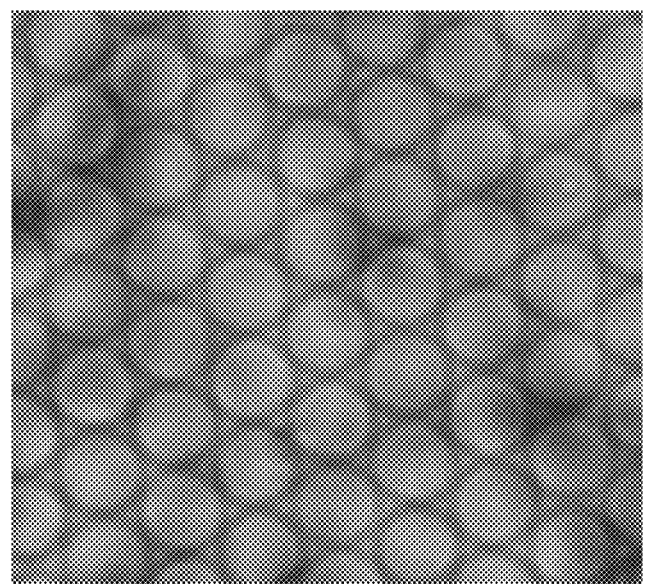
FIG. 5 shows images of droplet microparticles synthesized by the microfluidic flow focusing method.
Figure 6:
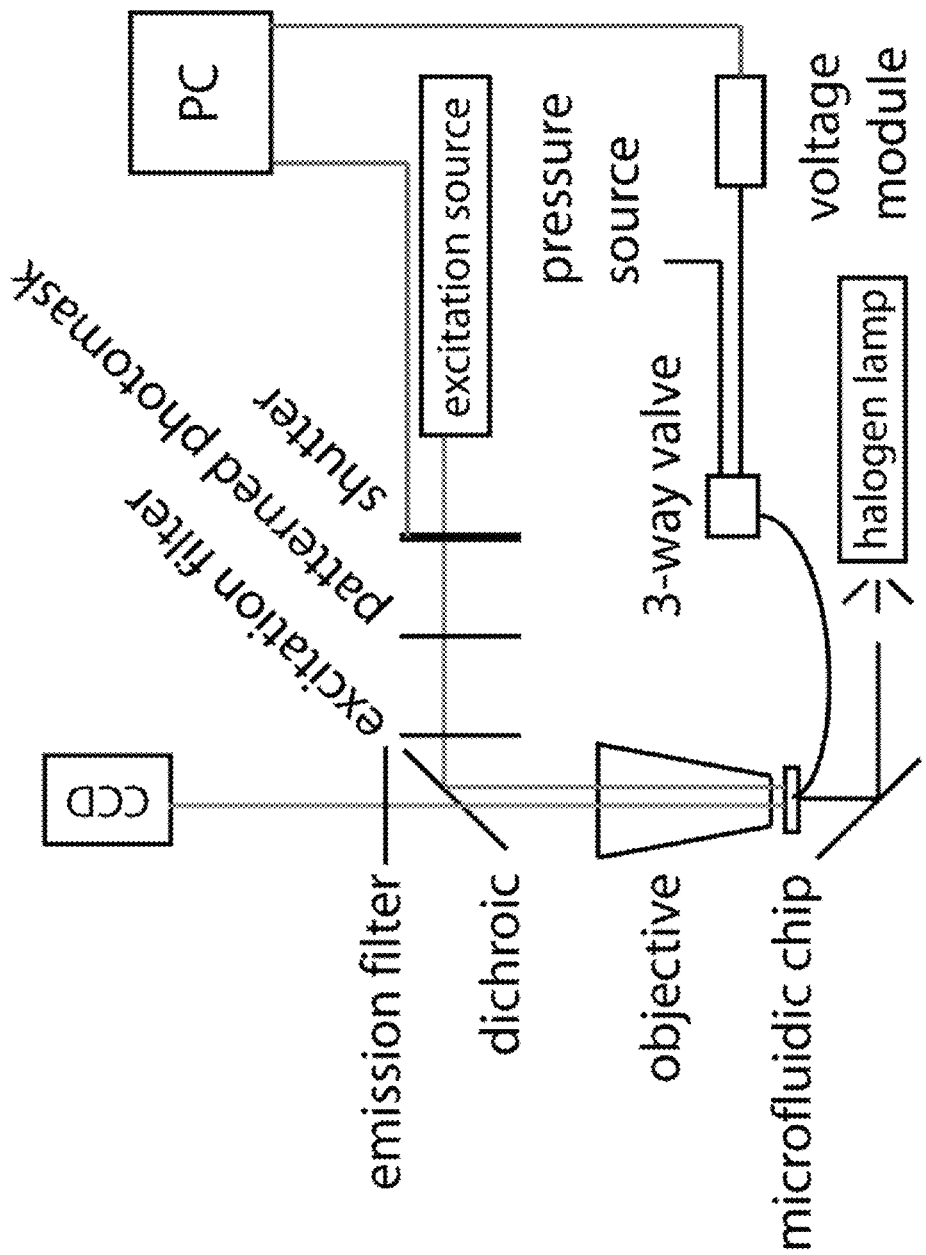
FIG. 6 shows the schematic of an apparatus for stop-flow lithography. An electronics control board controls a 3-way valve and shutter to provide synchronized stoppage of flow and UV photopolymerization of the PEG prepolymer mixture. A personal computer is utilized to program the control board. The PEG prepolymer mixture flows through the microfluidic chip, where the microparticles are photocured.
Figure 7:
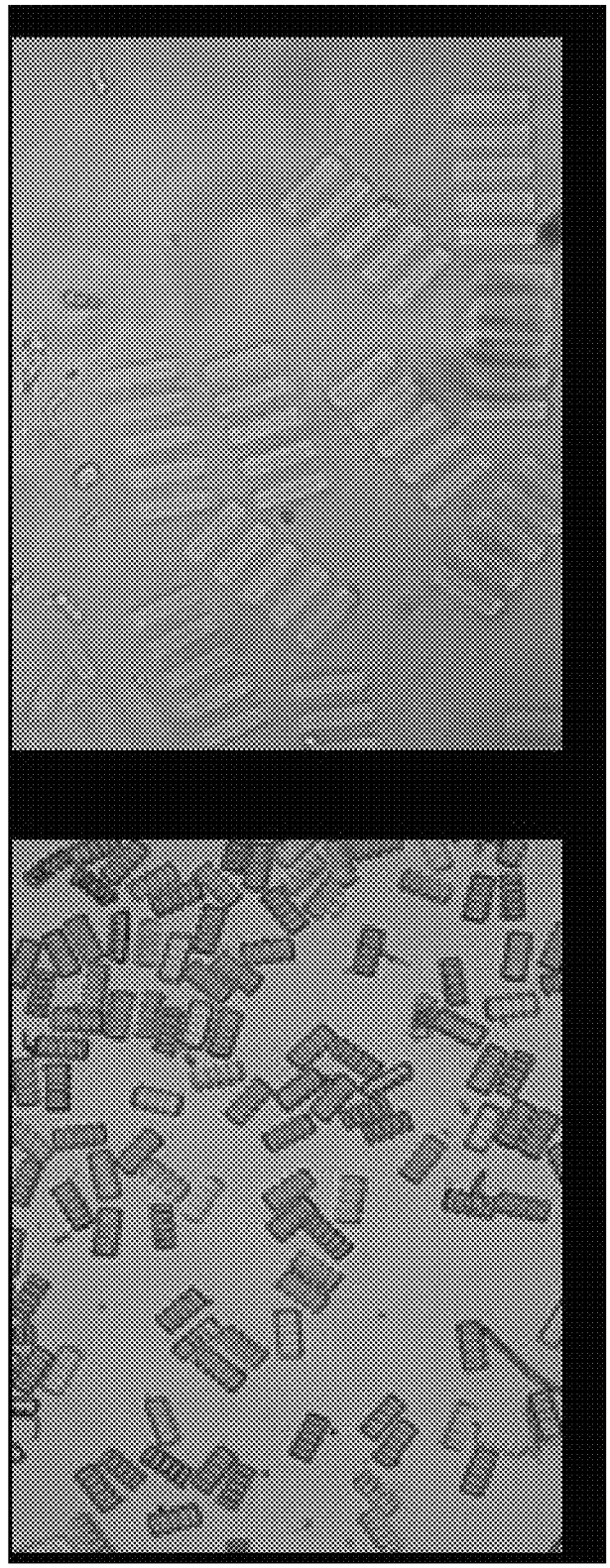
FIG. 7 shows images of examples of microparticles that can be synthesized by stop-flow lithography.
Figure 8:
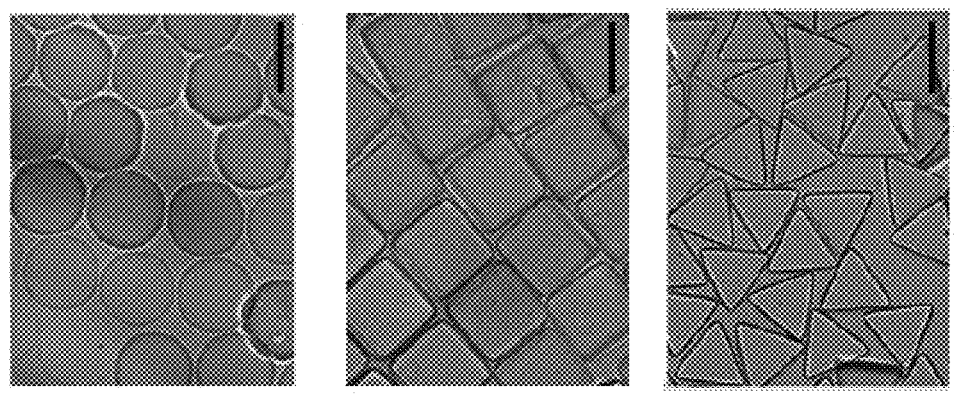
FIG. 8 shows a glass slide method of fabricating PEG microparticles. A droplet of the PEG prepolymer solution is dropped onto a PDMS-coated slide. A PDMS-coated photomask is placed on top of the solution and UV light transmitted through the photomask. The PEG microparticles are flushed from the surfaces and collected for analysis.
Figure 8:
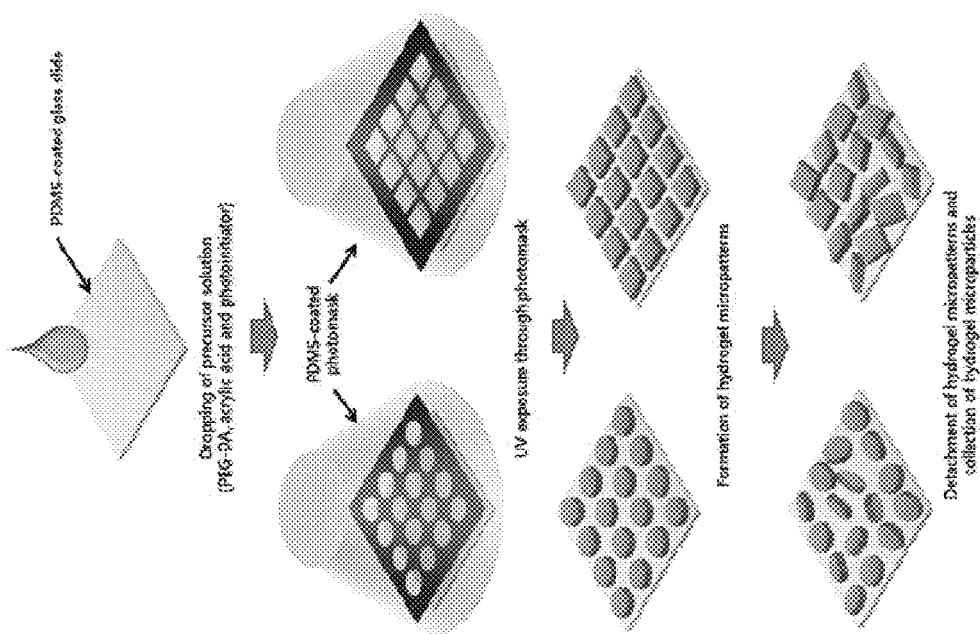

Non-amine chemistries can be utilized to conjugate biomolecules to monodisperse PEG microparticles synthesized by droplet formation, stop-flow lithography, slide-based UV exposure, or another PEG microparticle synthesis approach. These non-amine chemistries include the use of sulfhydryl groups, azide, or alkyne-based chemistries.

The use of thiol reactive or azide/alkyne chemistries for hydrogel PEG microparticle synthesis avoids the ready hydrolysis of amine/amine-based chemistries. Thiol reactive PEGs include those with maleimide (MAL), vinyl sulfone (VS), iodoacetamide (IA), and orthopyridyl disulfide (OPD). Heterobifunctional versions of these PEG molecules, for instance, ACRYL-PEG-VS or ACRYL-PEG-IA or ACRYL-PEG-OPD can be utilized to anchor the functional group within the matrix of the PEG microparticle. Multi-arm versions of the PEG molecules can also be utilized, as long as there is one ACRYL group and one functional group for reacting with a thiol.

While it is not as desirable, these functional groups can still be utilized without a reactive double bond acrylate group. This approach relies on entrapment of the reactive molecule within the PEG matrix. This approach is not a covalent linkage, but can be utilized if the molecular weight of the reactive molecule is large.

Azide (AZ)/alkyne (ALK) chemistry (commonly known as click chemistry) can also be used to bypass the limitations of traditional amine-based coupling methods for microparticles. Click chemistry is efficient, stereospecific, high-yield, and biocompatible. The use of ACRYL-PEG-AZ or ACRYL-PEG-ALK within the matrix of PEG microparticles enables the ready addition of a highly stable and selective functional group for functionality. As long as the corresponding biomolecule as an azide or alkyne group, the reaction can proceed quickly to enable the development of a stable covalent bond between the microparticle and the biomolecule. Other types of click chemistries can be utilized besides azide/alkyne combinations.

Regardless of the fabrication method, the chemistries described remain stable with numerous aqueous washes after particle synthesis. For instance, the maleimide functionality is stable, but is pH sensitive. It is 1000-fold more reactive towards sulfhydryl groups at pH 7 than amines. However, at pH>8.5, maleimide groups favor primary amines. At pH>8.0, hydrolysis can also occur which can decrease the half-life of the group. It is therefore desirable to wash the maleimide-functionalized particles with buffers that have a pH 6.5-7.5. Other types of chemistries have unique conditions where they are stable to hydrolysis.

The use of these non-amine chemistries allows for thorough manipulation of the microparticles. In particular, the microparticles often require multiple aqueous wash steps to resuspend them in a buffer of interest. The chemistry for biomolecule coupling needs to be stable during all these washes in order to have a high coupling efficiency. In one embodiment, a heterobifunctional PEG molecule, ACRYL-PEG-maleimide (MAL), is incorporated into the PEG photopolymerization mixture. The use of a maleimide group increases the stability of the functional group in aqueous environments, thereby prolonging the time for microparticle washing and manipulation. This mixture includes 10-90% PEG-DA (MW 770, Sigma Aldrich), 1-10% 2-hydroxy-2-methyl-1-phenyl-propan-1-one photoinitiator, 10-50% ACRYL-PEG-MAL (MW 3500), and distilled water. The solution is vortexed vigorously to ensure good mixing. This mixture is then utilized for the UV polymerization reaction. After the particles are synthesized, the particles are pelleted by low-speed centrifugation at 2000 rpm and washed and resuspended in the reaction buffer of choice. For instance, tier coupling to half antibodies, the microparticles are washed five times with 1 mL PBST with 10 mM EDTA. This is the reaction buffer of the half antibodies to the microparticles. The half antibody mixture is prepared by reduction with 2-mercaptoethylamine at 25-50 mM in a reaction buffer of 1×BupH PBS 1×EDTA (100 mM phosphate, 0.15M NaCl, 10 mM EDTA, pH 7.2) for 30-90 minutes at 37° C. The reduced half antibodies are purified by spin column or dialysis. The half antibodies are incubated with the maleimide functionalized microparticles overnight at room temperature. Optionally, the unreacted maleimide groups are quenched with cysteine, which contains excess sulfhydryl groups. The antibody functionalized microparticles are then washed in the desired buffer and are ready for use.

One approach for the synthesis of microparticles is through the generation of microfluidic droplets. This approach utilizes a microfluidic device that is fabricated with PDMS. The PDMS device is fabricated utilizing an SU-8 master mold. The microfluidic device is fabricated by replica molding. A mixture of PDMS prepolymer and curing agent (10:1, Sylgard 184, Dow Corning Co) is mixed, degassed, and poured onto the SU-8 master and cured at 65° C. The PDMS replica is bonded to a procured PDMS spin-coated glass slide. The dimensions of the channel are 200 μm width by 100 μm depth. The geometry of the channel is in the form where hexadecane can be utilized as the sheath to 2D focus a PEG mixture that can be utilized to form droplets. The PEG mixture has the desired functional groups for each coupling of biomolecules. The hexadecane phase has sorbitan monooleate (Span 80), a surfactant that decreases surface tension and allows for droplet formation. Microsyringe pumps (Harvard Apparatus PHD2000, USA) are utilized to precisely control the fluid flow in the continuous hexadecane/Span 80 phase and also the disperse PEG mixture phase. After droplet formation, the droplets are photopolymerized with UV light from a mercury arc lamp. The UV light is well-optimized to irradiate a specific region of the channel. By changing the Span 80 concentration, different droplet sizes can be synthesized. The microparticles are washed and resuspended in the desired reaction buffer. Droplet synthesis offers the advantages of high-throughput microparticle production. Furthermore, this approach results in highly uniform particles with a narrow distribution.

In a second method of hydrogel microparticle production, stop-flow or continuous flow lithography is utilized. In stop-flow lithography, the PEG mixture is introduced into a microfluidic device with a straight channel, with a depth consistent with the desired particle height. With the use of a valve and an electronically controlled shutter, the flow of the PEG mixture is stopped, then the shutter opened, allowing UV light to go through a photomask to pattern the PEG prepolymer mixture. The flow is turned back on to move the polymerized particles downstream, allowing the cycle to be repeated again. The polymerization is performed on a Zeiss Axio Observer inverted microscope with a field stop position for the photomask, which is designed in AutoCAD and printed on a high-resolution printer (CAD/ART Services, OR). Exposure times are on the order of 50-100 ms, depending on the strength of the arc lamp and the number of hours on it. The stop-flow lithography approach is lower throughput than droplet formation, but offers the advantage of having different shapes for multiplexing.

Slide-based fabrication of PEG microparticles requires a UV light source and no pumps or fluidics. This is the simplest of the particle fabrication methods. The PEG prepolymer mixture is dropped onto a glass slide coated with cured PDMS. It is spread by place a PDMS-coated photomask on top of it. UV light is transmitted through the photomask at 300 mW/cm$^2$ to cure the particles. The final hydrogel particles are obtained by flushing the PDMS-coated glass slide and the photomask to release the microparticles. The particles are washed to remove any unreacted molecules from the particles and resuspended in the reaction buffer of choice.

Those skilled in the art will recognize, or be able to ascertain using no more than routine experimentation and/or engineering, many equivalents to the specific embodiments of the invention described herein. The scope of the present invention is not intended to be limited to the above Description, but rather is as set forth in the claims that follow the reference list.

The invention claimed is:

1. A microparticle comprising:
    a polyethylene glycol (PEG) body, and
    a biomolecule, wherein the biomolecule is conjugated to the PEG body using a non-amine chemistry incorporated into the PEG body in a covalent manner,
    wherein the microparticle is UV cured.

2. The microparticle of claim 1 wherein the non-amine chemistry is selected from a group consisting of sulfhydryl groups, thiol reactive, and click-based chemistries.

3. The microparticle of claim 2 wherein the non-amine chemistry is selected from the group consisting of maleimide (MAL), vinyl sulfone (VS), iodoacetamide (IA), ACRYL-PEG-VS, ACRYL-PEG-IA, and multi-arm PEG having at least one acryl group and at least one functional group for reacting with a thiol, wherein the acryl group is selected from the group consisting of methoxyacrylate, methacrylate, and acrylate.

4. The microparticle of claim 2 wherein the non-amine chemistry is selected from the class of ACRYL-PEG-CLICK.

5. The microparticle of claim 4 wherein the non-amine chemistry is selected from the group consisting of ACRYL-PEG-ALK and ACRYL-PEG-AZ.

6. The microparticle of claim 1 wherein the PEG body is elongated.

* * * * *